United States Patent [19]

Smith

[11] Patent Number: 4,460,702

[45] Date of Patent: Jul. 17, 1984

[54] CATALYST PRECURSOR

[75] Inventor: William E. Smith, Schenectady, N.Y.

[73] Assignee: General Electric Company, Selkirk, N.Y.

[21] Appl. No.: 429,713

[22] Filed: Sep. 30, 1982

Related U.S. Application Data

[63] Continuation of Ser. No. 309,355, Oct. 7, 1981, , which is a continuation-in-part of Ser. No. 182,679, Aug. 29, 1980.

[51] Int. Cl.$^3$ .................. B01J 23/02; B01J 23/34; B01J 31/02
[52] U.S. Cl. .................................................. 502/150
[58] Field of Search ................. 252/430, 471; 502/150

[56] References Cited

U.S. PATENT DOCUMENTS 3,972,836  8/1976  Van Sorge ..................... 252/471

Primary Examiner—W. J. Shine

[57] ABSTRACT

Catalytic ortho-alkylation process which comprises reacting a phenolic compound with an alcohol in the presence of a catalyst composite comprising a calcination residue derived from a catalyst preform prepared from an admixture of (1) a magnesium carbonate and/or magnesium hydroxide, (2) a manganese compound, and (3) a complex of poly(2,6-dimethyl-1,4-phenylene oxide) and a solvent selected from dichloromethane, dibromomethane, bromochloromethane and mixtures thereof.

8 Claims, No Drawings

CATALYST PRECURSOR

This application is a continuation of co-pending application Ser. No. 309,355 filed Oct. 7, 1981, which is a continuation-in-part of application Ser. No. 182,679 filed Aug. 29, 1980.

BACKGROUND OF THE INVENTION

This invention relates to a catalytic process for the preparation of ortho-alkylated phenols which comprises reacting a phenolic compound with an alcohol in the presence of a catalyst composite comprising a calcination residue derived from a catalyst preform prepared from an admixture of (1) a magnesium carbonate and/or a magnesium hydroxide, (2) a manganese compound, and (3) a complex of poly(2,6-dimethyl-1,4-phenylene oxide) and a solvent selected from dichloromethane, dibromomethane, bromochloromethane and mixtures thereof.

DESCRIPTION OF THE PRIOR ART

Van Sorge in U.S. Pat. No. 3,843,606—issued Oct. 22, 1974, describes the preparation of ortho-alkylated phenols using a porous magnesium oxide powder catalyst bonded with an inert organic cellulosic polymeric binder, e.g. the magnesium oxide catalyzed alkylation of phenols with methanol to form ortho-cresol, 2,6-xylenol, and 2,4,6-mesitol at temperatures of at least 460° C. without reduction in catalytic activity for periods in excess of 500 hours.

Pecak in U.S. Pat. No. 3,962,126—issued June 8, 1976 describes the reactivation of a carbonized magnesium oxide-manganese oxide alkylation catalyst by contacting a deactivated catalyst with oxygen and water at a temperature below 300° C. to restore ortho-alkylation catalyst activity.

Van Sorge in U.S. Pat. No. 3,972,836—issued Aug. 3, 1976 describes the ortho-alkylation of phenols employing catalysts derived from the calcination of blends of magnesium oxide, manganese oxides and water. The improved catalytic alkylation process is described as effective at temperatures as low as 420° C. preferably employed at 460° C. Effective catalyst activity is reported as being in excess of 1,000 hours.

The catalytic process of this invention permits ortho-alkylation of phenols continuously at moderate temperatures at high selectivity and high conversion efficiencies when compared to the catalytic processes of the prior art.

DESCRIPTION OF THE INVENTION

This invention embodies a catalytic process for the preparation of ortho-alkylated phenols which comprises reacting a phenolic compound with an alcohol in the presence of a catalyst composite comprising a calcination residue derived from a catalyst preform prepared from an admixture of (1) a magnesium carbonate and/or a magnesium hydroxide, (2) a manganese compound, and (3) a complex of poly(2,6-dimethyl-1,4-phenylene oxide) and a solvent selected from dichloromethane, dibromomethane, bromochloromethane and mixtures thereof.

The phenolic compounds are well-known and include any of the phenolics described by Van Sorge in U.S. Pat. No. 3,972,836 whose descriptions are incorporated herein by reference. Illustratively, phenolics include phenol itself, i.e. hydroxy benzene, ortho-cresol, ortho-phenyl phenol, ortho-ethyl phenol, and phenols in which there are alkyl or aryl groups in the meta- and para-positions. The phenolic compounds can be represented by the formula:

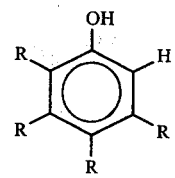

where each R is a monovalent substituent selected from the group consisting of hydrogen, alkyl, e.g., $C_1$–$C_{12}$ alkyl, phenyl and alkyl-substituted phenyl, e.g., $C_1$–$C_{12}$ alkyl-substituted phenyl.

The alcohols are also well-known and include any of those described by Van Sorge and include alkyl alcohols, e.g. saturated aliphatic alcohols, such as methyl, ethyl, propyl, isopropyl, butyl, isobutyl, tert.-butyl, amyl isoamyl, hexyl, heptyl, octyl, nonyl, decyl, undecyl, lauryl, cetyl, cyclohexyl and the like, alcohols. Especially preferred are alcohols containing up to 6 carbon atoms.

The calcination residue is derived from a catalyst preform composite admixture formed from a combination of (1) a magnesium carbonate and/or magnesium hydroxide, (2) a manganese compound, (3) a complex of poly(2,6-dimethyl-1,4-phenylene oxide) and a solvent selected from dichloromethane, dibromomethane, bromochloromethane, including mixtures thereof, which is subsequently calcined at elevated temperatures to form an active catalyst composite.

In a preferred embodiment, the magnesium-manganese component of the catalyst preform is derived from a magnesium carbonate-magnesium hydroxide and manganese hydroxide blend prepared by precipitating manganese hydroxide in the presence of "basic" magnesium carbonate, e.g. $xMgCO_3 \cdot Mg(OH)_2 \cdot xH_2O$—where independently each x is a number average of from about 3 to about 5—from a water soluble salt of manganese in the presence of a base. The resulting slurry of $xMgCO_3 \cdot Mg(OH)_2 \cdot xH_2O$ and $Mn(OH)_2$ is subsequently washed free by any residual water soluble deleterious cations or anions, dried and formed into a powder.

The specific poly(2,6-dimethyl-1,4-phenylene oxide) which is employed is well known for its unique ability to dissolve and form a crystalline adduct, i.e. a "complex", with dichloromethane—more commonly known as methylene chloride, dibromomethane, bromochloromethane including mixtures thereof, in accordance with the description and teachings—incorporated herein in their entirety by reference—of A. Factor et al. described in "Polymer Letters" Vol. 7, pp 205–209 (1969) and U.S. Pat. No. 3,644,227. Any polyphenylene oxide resin which contains sufficient 2,6-dimethyl-1,4-phenylene oxide recurring units of the formula

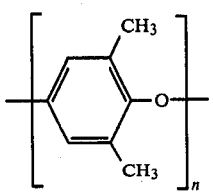

(I)

within the polymer skeletal structure, n being a number at least equal to about 10, which dissolves and forms complexes with dichloromethane, dibromomethane, bromochloromethane and mixtures thereof can be employed. Presently preferred poly(2,6-dimethyl-1,4-phenylene oxides) are homopolymers of the above formula having an intrinsic viscosity of at least about 0.40 dl/g measured in chloroform at 25° C.

In the preparation of the above-mentioned catalyst preform composite, the components consisting of magnesium carbonate and/or magnesium hydroxide, a manganese compound and a poly (2,6-dimethyl-1,4-phenylene oxide), all in particulate form, are thoroughly dispersed in any amount and proportion desired of the final catalyst preform composite, in a member of the solvent complexing class i.e. dichloromethane, dibromomethane, bromochloromethane or any mixture thereof.

In general, a best mode of preparation entails dry blending of the magnesium-manganese catalyst components and polyphenylene oxide, pulverizing the resulting admixture into particulate form, with subsequent dispersion thereof in a complex forming solvent. As the polyphenylene oxide dissolves in the solvent a polyphenylene oxide-solvent complex (solid phase) forms which is in mobile equilibrium with a polyphenylene oxide-solvent (liquid phase) in accordance with the above-referenced teachings of A. Factor. The resulting solid phase constituents, e.g. magnesium-manganese and crystalline adduct—containing approximately two moles of solvent, e.g. methylene chloride, per mole of 2,6-dimethyl-1,4 phenylene oxide recurring units—dispersed in the liquid solvent phase are subsequently separated from the liquid phase by routine filtration and/or evaporation techniques to provide the unique finitely uniformly dispersed admixture of solid magnesium-manganese-polyphenylene oxide-solvent complex of the catalyst preform components.

Any amount, type or proportion of any well known effective prior art ortho-alkylation catalyst as well as those described in Smith and Battista's copending U.S. application Ser. No. 163,486, filed June 17, 1980, now abandoned, which contain, e.g., magnesium and/or manganese compounds, can be used in highly dispersed form with a solid phase polyphenylene oxide-solvent complex. Generally preferred catalyst preforms contain, on a weight basis, 70 to 99% of an effective ortho-alkylation catalyst species, e.g., a mixture of magnesium-manganese components, and 30 to 1% of a polyphenylene oxide-solvent complex. The finely dispersed solid catalyst preform constituents—after removal of the residual solvent contained within the crystalline adduct of the polyphenylene oxide-solvent complex, e.g., by heating after conventional shaping of the catalyst preform into catalyst pellets at room temperatures or higher—are employed in the practice of the process described herein.

In the practice of this invention the ortho-alkylation of phenols comprises reacting a phenolic compound with an alcohol carried out by charging the unique catalyst preforms of this invention to an alkylation catalyst bed. The catalyst preforms are subsequently activated via calcination at elevated temperatures, e.g., temperatures generally of from 300° C. to 500° C. or even higher, and the ortho-alkylation of phenolics is subsequently or concurrently carried out according to any of the well known state-of-the-art process parameters.

The pressures used in carrying out the instant reaction can be varied widely and are not critical. Depending upon the temperatures used, the ratio and kind of ingredients, the apparatus, etc., either atmospheric, superatmospheric and even subatmospheric pressures can be employed. As is well known increases of pressure during the alkylation reaction usually accelerated the rate of reaction. Although the examples in the instant application are carried out at atmospheric pressures this was in part due to the simplicity of the apparatus. It is contemplated that in large scale commercial production with more sophisticated equipment to effect certain results, such as rate of reaction, yield, purity, etc., superatmospheric pressures, ranging from atmospheric pressure to as high as 60–100 psig or higher may be employed without departing from the scope of the invention.

GENERAL ORTHO-ALKYLATION PROCESS PROCEDURE

The following general procedure was used to evaluate and compare the catalysts described herein. A series of 2,6-xylenol alkylations were carried out contrasting the invention catalysts with commercially available "prior art" catalyst composites and catalyst composites described in the aforesaid Smith and Battista copending patent application. The description in this application is incorporated herein in its entirety by reference.

In the following examples the alkylation reaction was carried out under the following general reaction conditions.

Phenolic feedstocks including water were pumped from a reservoir through a ¼" stainless steel tube into a vertical vaporizer, i.e., at 12" long stainless steel tube having a 0.8" I.D. and a 1" O.D. The vaporizer was partially immersed in a bath of fused salt to a depth of about 6". Vaporized feedstock was fed into a 24" long stainless steel tube reactor having a 0.8" I.D. through a 1" length of ¼" I.D. stainless steel pipe located 5½" above the bottom of the vaporizer and attached to the reactor 13" above the bottom of the reactor. The reactor was immersed in a fused salt bath to a depth of about 14". The reactor temperature, estimated as the equivalent of the salt bath temperature, was measured throughout each alkylation reaction.

The catalyst bed was filled to a constant volume of 110 milliliters with pelletized catalyst which filled the reactor tube to a depth of 12". Feedstock and water vapors were fed into the top of the catalyst bed and reaction product vapors left the bottom of the reactor through a ⅜" I.D. stainless steel tube. The product vapors were passed to a water-cooled condenser-receiver, and the condensed vapors containing any unreacted feedstock as well as the desired end-product 2,6-xylenol were analyzed by VPC techniques. Non-condensed gases containing hydrogen, carbon monoxide, carbon dioxide, methane and ethane were scrubbed and passed through a wet-test meter to determine their volume.

A resume of the process parameters and results associated with the ortho-alkylation process of this invention employing the catalysts of this invention as well as other comparative catalyst compositions is set out in the Tables hereafter. The best mode of preparing the catalysts within the scope of this invention is also described herein.

EXAMPLE I

Catalyst Preparation

A slurry of 289.3 grams of Mg (OH)$_2$ in 1250 ml. of distilled water was combined with 40.0 grams of Mn (NO$_3$)$_2$, diluted to 250 ml. with distilled water over approximately a 4-minute time period. The resulting slurry was stirred for 2 hours and filtered. The resulting wet cake was resuspended with 750 ml. of distilled water and filtered. The "resuspension" procedure was repeated four more times. The final "resuspension" was carried out in 750 ml. of acetone. The resulting wet cake filtrate was dried overnight under vacuum at approximately 100° C. oven and ground to a fine powder. The powder was high-shear horizontal roll mill blended for 15 minutes with sufficient polyphenylene oxide to provide 80 parts by weight of Mg (OH)$_2$ co-precipitated with Mn (OH)$_2$ and 20 parts by weight of polyphenylene oxide. The resulting powder admixture was thoroughly wet by mixing with 500 ml. of methylene chloride, and dried for 2 hours in a 32.2° C. vacuum oven. After drying the resulting admixture was ground to a fine powder and tabletted to ⅛"×3/16" catalyst pellets in a tableting press.

CATALYST AND PROCESS TESTING

The reactor—after charging with catalyst pellets—was capped and immersed in the salt bath at 370° C. The catalyst was pre-heated while nitrogen was passed through the bath-heated catalyst bed at a volumetric rate corresponding to 2 SCFH (standard cubic feet per hour) for 15 minutes.

Immediately following the 15-minute period, under continuous process reaction conditions, liquid feedstock which contained methanol, phenol, ortho-cresol and water, was continuously fed to the reactor at a rate of 228 ml/hour throughout a 416 hour test. The resulting feed vapors were continuously passed through the catalyst as described above. The conditions and results of the test are set forth in Table I.

TABLE I

| Feed Composition | | |
|---|---|---|
| Molar Ratio Methanol to Phenolic Compounds | 4:1 | |
| Molar Ratio Phenol to Ortho-Cresol | 60:40 | |
| Wt. % Water in Feed | 23 | |
| Operating Conditions | | |
| Temperature (°C.) | 455–479 | |
| LHSV (hr.$^{-1}$)[1] | 2.07 | |
| Pressure (psig) | 0 | |
| Phenolic Distribution (wt. %) | 200 hrs.[2] | 416 hrs.[3] |
| o-cresol | 25.32 | 31.98 |
| 2,6-xylenol | 70.59 | 63.56 |
| 2,4,6-mesitol | 2.08 | 1.05 |
| Phenol | 2.02 | 3.42 |
| Off Gas (Wt. %) | 0.420 | 0.580 |

[1]LHSV is the liquid hourly space velocity and defines the volume of liquid per volume of catalyst per hour.
[2]Temperature at the indicated elapsed in hours time was 455° C.
[3]Temperature at the indicated elapsed in hours time was 479° C.

EXAMPLE II

Catalyst Preparation

A slurry of 453.2 grams of "basic" MgCO$_3$ in 2000 ml. of distilled water was combined with 40.0 grams of Mn(NO$_3$)$_2$, diluted to 500 ml. with distilled water over approximately a 4-minute time period. 10.8 grams of a 50% caustic NaOH solution diluted to 500 ml. with distilled water was added to the resulting admixture over approximately 4 minutes, followed by stirring for one hour at room temperature. The slurry was vacuum filtered, washed with 1500 ml. of distilled water, resuspended by homogenizing in water and vacuum filtered again. The "resuspension" procedure was repeated four more times. The final "resuspension" was carried out in 1250 ml. of acetone. The filtrate was dried overnight under vacuum in a 120° C. oven and ground to a fine powder. The powder was blended with sufficient polyphenylene oxide to provide 80 parts by weight of "basic" MgCO$_3$ co-precipitated with Mn(OH)$_2$ and 20 parts by weight of polyphenylene oxide. 600 ml. of methylene chloride was added to the 80:20 blend to form a uniformly moist paste. The paste was dried overnight under vacuum in a 50° C. oven. The dried powder was ground to a fine powder, tabletted to 1/16"×3/16" tablets in a tableting press.

CATALYST AND PROCESS TESTING

The reactor—after charging with catalyst pellets—was capped and immersed in the salt bath at 370° C. The catalyst was pre-heated by passing nitrogen through the bath-heated catalyst bed at a volumetric rate corresponding to 2 SCFH (standard cubic feet per hour) for 15 minutes.

Immediately following, under continuous process reaction conditions, liquid feedstock which contained methanol, phenol, ortho-cresol and water, was continuously fed at a rate of 228 ml/hour throughout a 504-hour test. The resulting feed vapors were continuously passed through the catalyst as described above. The conditions and results of the test are set forth in TAble II.

TABLE II

| Feed Composition | | | |
|---|---|---|---|
| Molar Ratio Methanol to Phenolic Compounds | 4:1 | | |
| Molar Ratio Phenol to Ortho-Cresol | 60:40 | | |
| Wt. % Water in Feed | 23 | | |
| Operating Conditions | | | |
| Temperature (°C.) | 455—455 | | |
| LHSV (hr.$^{-1}$) | 2.07 | | |
| Pressure (psig) | 0 | | |
| Phenolic Distribution (wt. %) | 198 hr.[2] | 504 hr.[3] | TWA[4] |
| o-cresol | 15.16 | 28.86 | 23.67 |
| 2,6-xylenol | 78.98 | 66.54 | 69.54 |
| 2,4,6-mesitol | 4.34 | 3.27 | 3.90 |
| Phenol | 1.27 | 3.33 | 2.95 |
| Off Gas (Wt. %) | 0.490 | 0.335 | 0.337 |

[1]LHSV is the liquid hourly space velocity and defines the volume of liquid per volume of catalyst per hour.
[2]Temperature at the indicated elapsed time in hours was 455° C.
[3]Temperature at the indicated elapsed time in hours was 455° C.
[4]Time-weighted average of numerous values obtained at generally uniform intervals throughout the 504-hour test.

COMPARATIVE PRIOR ART CATALYST PROCESS DATA

Prior art commercial catalyst composites containing, on weight percent basis, typically, 65% MgO:31%

Mg(OH)$_2$:4% Mn$_2$O$_3$ which had been formed into 3/16" dia.×3/16" long cylindrical pellets, and which after pelletizing had been heated for 6 hrs., at 700° F., were evaluated as described in the General Ortho-Alkylation Process Procedure.

The reactor—after charging with catalyst pellets—was capped and immersed in a salt bath at 370° C. The catalyst was pre-heated by passing nitrogen through the bath-heated commercial catalyst bed at a volumetric rate corresponding to 2 SCFH (standard cubic feet per hour) for 15 minutes.

Immediately following the 15-minute catalyst preheat, under continuous process reaction conditions, liquid feedstock which contained methanol, phenol, ortho-cresol and water, was continuously fed at a rate of 190 ml/hour throughout a 456-hour test. The resulting feed vapors were continuously passed through the catalyst as described above. The conditions and results of the test are set forth in Table III.

TABLE III

| Feed Composition | | |
|---|---|---|
| Molar Ratio Methanol to Phenolic Compounds | 4:1 | |
| Molar Ratio Phenol to Ortho-Cresol | 60:40 | |
| Wt. % Water in Feed | 3 | |
| Operating Conditions | | |
| Temperature (°C.) | 487–500 | |
| LHSV (hr.$^{-1}$) | 1.72 | |
| Pressure (psig) | 0 | |
| Phenolic Distribution (wt. %) | 200 hrs.[2] | 456 hrs.[3] |
| o-cresol | 31.99 | 45.85 |
| 2,6-xylenol | 60.30 | 34.95 |
| 2,4,6-mesitol | 2.04 | 0.69 |
| Phenol | 5.33 | 18.18 |
| Off Gas (Wt. %) | 0.710 | 0.530 |

[1]LHSV is the liquid hourly space velocity and defines the volume of liquid per volume of catalyst per hour.
[2]Temperature at the indicated elapsed in hours time was 487° C.
[3]Temperature at the indicated elapsed in hours time was 500° C.

In a preferred embodiment of the process of this invention the catalyst composite contains a major proportion of magnesium in the form of magnesium carbonate and a minor proportion of a manganese compound wherein the combination of catalyst components are substantially free of deleterious water-soluble cations or anions, and further wherein the catalyst composites are formed in situ into active ortho-alkylation catalyst species during the ortho-alkylation of phenolic compounds with alcohols.

What I claim as new and desire to secure by Letters Patent of the United States is:

1. A catalyst precursor capable of being calcined to form an active catalyst, said catalyst precursor formed by
   (a) providing a mixture comprising a slurry of a magnesium-containing compound in water and a manganese-containing compound;
   (b) adding a caustic solution to said mixture to form a precipitate;
   (c) mixing said precipitate with polyphenylene oxide to form a blend;
   (d) adding a solvent selected from the group consisting of methylene chloride, dibromomethane, bromochloromethane, and mixtures thereof to said blend in an amount to wet thoroughly said blend.

2. The catalyst precursor of claim 1 wherein said magnesium-containing compound is provided by magnesium hydroxide.

3. The catalyst precursor of claim 1 wherein said magnesium-containing compound is provided by "basic" magnesium carbonate.

4. The catalyst precursor of claim 1 wherein said magnesium-containing compound is provided by a mixture of "basic" magnesium carbonate and magnesium hydroxide.

5. The catalyst precursor of claim 1 wherein said manganese-containing compound is manganese nitrate.

6. The catalyst precursor of claim 1 wherein said polyphenylene oxide is poly(2,6-dimethyl-1,4-phenylene oxide).

7. The catalyst precursor of claim 1 wherein said methylene chloride is added to said blend in an amount sufficient to form a complex between said polyphenylene oxide and said solvent.

8. The catalyst precursor of claim 1 wherein said catalyst precursor is a solid mixture comprising magnesium, manganese, said solvent and poly(2,6-dimethyl-1,4-phenylene oxide).

* * * * *